United States Patent [19]

Arndt et al.

[11] 4,246,196
[45] Jan. 20, 1981

[54] DIAMINOPHENYL UREAS

[75] Inventors: Otto Arndt, Hofheim am Taunus; Theodor Papenfuhs, Frankfurt am Main; Peter Böhme, Kelkheim; Wolfgang Tronich, Hofheim am Taunus; Bernhard Mees, Eppstein, all of Fed. Rep. of Germany

[73] Assignee: Hoechst AG., Frankfurt am Main, Fed. Rep. of Germany

[21] Appl. No.: 105,500

[22] Filed: Dec. 20, 1979

[30] Foreign Application Priority Data

Dec. 23, 1978 [DE] Fed. Rep. of Germany ....... 2855883

[51] Int. Cl.³ .......................................... C07C 127/19
[52] U.S. Cl. ..................................... 564/50; 548/305
[58] Field of Search ................................... 260/553 A

[56] References Cited

U.S. PATENT DOCUMENTS

| 3,149,032 | 9/1964 | Waring | 260/553 A X |
| 3,674,414 | 7/1972 | Kalopissis et al. | 260/553 A X |

FOREIGN PATENT DOCUMENTS

| 631007 | 10/1949 | United Kingdom | 260/553 A |
| 631025 | 10/1949 | United Kingdom | 260/553 A |

Primary Examiner—Thomas A. Waltz
Attorney, Agent, or Firm—Curtis, Morris & Safford

[57] ABSTRACT

Diaminophenyl ureas of the formula

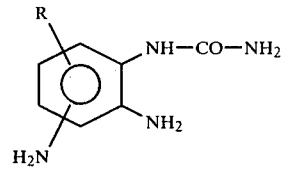

in which R is an inert substituent, are obtained from the corresponding dinitrophenyl urea by way of reduction, especially catalytic hydrogenation. Through a cyclization process, while splitting off ammonia, these ureas yield the corresponding aminobenzimidazolones, advantageously without an intermediate isolation of the diaminophenyl ureas.

10 Claims, No Drawings

DIAMINOPHENYL UREAS

The invention relates to diaminophenyl ureas which are useful for preparing 5-aminobenzimidazolones-(2), which, in turn, are intermediates for the preparation of azo pigments.

For the preparation of 5-aminobenzimidazolones-(2), several processes have been proposed:

The reduction of N-(2,4-dinitrophenyl)-ethylurethane to give N-(2,4-diaminophenyl)-ethyl-urethane and the cyclization of the latter to 5-aminobenzimidazolone-(2), while splitting off alcohol, have already been described in Chem. Ber. 17 (1884) 2631. However, due to the complicated preparation of the pure starting product and the unsatisfactory yield and purity of the final product, the above process has not become relevant in practice.

From Monatshefte f. Chemie 107 (1976) 1307 to 1310, the nitration of benzimidazolone-(2) to yield 5-nitrobenzimidazolone-(2) is known. This latter product may be converted into 5-aminobenzimidazolone-(2) by the reduction of the nitro group. This process has the drawback, however, that the formation of isomers and benzimidazolones-(2) nitrated to a higher degree cannot be completely avoided. Besides, the nitration represents an additional process step which involves the corresponding technical expenditure.

A different approach to the preparation of 5-nitrobenzimidazolone-(2) has been described in J. Chem. Soc. C (1971) 1139, which involves a thermolysis of 2,4-dinitrophenyl glycine. However, due to its poor yield and the formation of considerable amounts of unknown decomposition products, this process is of no interest in practice.

Finally, it is known from German Offenlegungsschrift No. 27 25 957 that 1,2-diamino-4-nitro-benzene can be condensed in organic media with urea to give 5-nitrobenzimidazolone-(2) which may then be reduced, for example with iron, to yield 5-aminobenzimidazolone-(2). However, the preparation of 1,2-diamino-4-nitrobenzene is rather complicated and difficult owing to the partial reduction of one nitro group only in 2,4-dinitroaniline with sodium sulfide and is therefore of no interest in practice, either.

The cyclization reaction of 2-aminophenyl urea to give benzimidazolone has been known from Gazz. Chim. Ital. 49I (1919) 22 and that of 2-amino-4- or -5-carboxyphenyl urea to give benzimidazolone-5-carboxylic acid was described in Ann. 291, 327 (1896). However, the 5-aminobenzimidazolones desired are also obtained via a nitration of the benzimidazolones and subsequent reduction of the nitrobenzimidazoles, which again involves two additional operations and the above-mentioned problems. It is a remarkable fact that in the synthesis described a dinitro compound is prepared first, from which a nitro group is split off, however, prior to the reduction.

Thus, the cyclization reaction of suitable diaminophenyl ureas, which should lead in a simple and direct manner to the desired aminobenzimidazolones, has not yet been described in literature.

The subject of the present invention are compounds of the formula

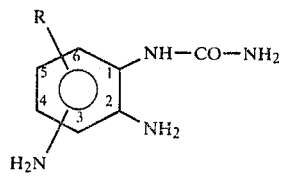

in which R is hydrogen, halogen, lower alkyl, lower alkoxy, phenyl, phenoxy or a fused benzene ring, a process for preparing these compounds, which comprises reducing a dinitrophenyl urea of the formula

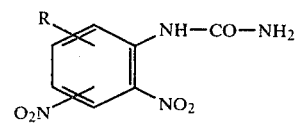

R being defined as above, and the use of the compounds of the invention for the preparation of aminobenzimidazolones of the formula

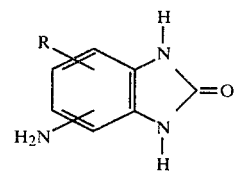

R being defined as above, through a cyclization reaction while splitting off ammonia, by heating in a liquid medium.

The term "lower" means groups containing 1 to 6, especially 1 to 4 carbon atoms.

The dinitrophenyl ureas employed as starting compounds are known from U.S. Pat. No. 2,826,611 and from J. pr. Ch. 110 (1925) 300 and may be obtained according to the processes described therein.

Thus, the invention may be illustrated by the general reaction scheme

![reaction scheme A]

(A)

-continued

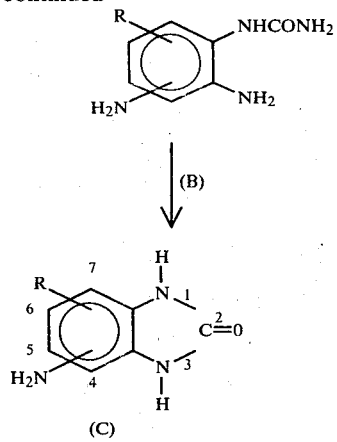

In this formula, R represents the above-mentioned inert substituents, preferably hydrogen, chlorine, methyl, methoxy or a fused benzene ring, the second amino group being present in the 6- or 4-position, in particular a substituent having one of the meanings given in Table I below:

Table I

| R | Position of the nitro group in formula A |
|---|---|
| H | 6 |
| H | 4 |
| 6-CH$_3$ | 4 |
| 6-Cl | 4 |
| 5-CH$_3$ | 4 |
| 5-OCH$_3$ | 4 |
| fused benzene ring in the 5- and 6-positions | 4 |

In principle, the diaminophenyl ureas obtained after the reduction of the dinitrophenyl ureas may be isolated and cyclized in the absence of the reducing agent - and with a reduction performed catalytically, also in the absence of the catalyst. However, according to a preferred variant of the process the cyclization reaction is carried out without the intermediate isolation of the diaminophenyl urea. Thus, the diaminophenyl ureas are generally characterized in the form of the corresponding benzimidazolones.

The reduction of the nitro groups may be effected in accordance with processes known from literature, for example with iron, however, catalytic hydrogenation being preferably employed.

Suitable reduction media or diluents are all organic or aqueous media or the mixtures thereof which are generally used in such cases; a particularly simple, inexpensive and thus preferred embodiment involves the use of water as reducing and cyclizing agent. In the catalytic reduction the pH value depends in particular on the type of catalyst employed, for example on the acid or alkali resistance of the latter. According to a preferred embodiment of the catalytic reduction there are used for example non-noble metal catalysts, especially nickel catalysts, and the pH value of the reduction medium is adjusted - optionally by adding appropriate buffer substances - in a way that it does not fall below 6 and does not reach a value substantially above 10, especially in the cyclization to give the aminobenzimidazolone-(2). The catalytic reduction is preferably carried out in the presence of a phosphate buffer system at pH 6 to 7; in the course of the cyclization, the pH rises to a value of from 8 to 10 due to the ammonia being set free.

However, the cyclization may also be executed at a pH of less than 8, preferably less than 6, if care is taken that the ammonia being formed is bound by means of an acid, in which process the pH may fall to about 1.

The catalytic reduction may of course also be carried out in the presence of noble metal catalysts, for example palladium or platinum catalysts, the pH value of the reduction mixture then possibly being also less than 6.

The hydrogen pressure, the reduction temperature and the reduction period are within the range which is common for the catalytic reduction of aromatic nitro compounds.

The cyclization of the diaminophenyl urea compounds may be carried out in the presence or absence of reducing agents and catalysts. According to a particularly simple and preferred embodiment of the process the cyclization is executed, for example, directly following the catalytic hydrogenation of the dinitrophenyl ureas in the hydrogenation autoclave, in which process the hydrogen is merely previously removed optionally from the gas space, for example by rinsing with nitrogen, however, while leaving the hydrogenation catalyst in the autoclave. The cyclization may be effected without pressure at a temperature of up to 100° C. or, preferably, at a temperature of more than 100° C. with a corresponding overpressure.

The duration of the cyclization reaction depends on the respective reaction temperature and is in the range of from 3 to 10 hours. The pH value of the reaction mixture corresponds at the beginning of the reaction to the pH of the reduction mixture and rises with the progress of the cyclization reaction up to 10 due to the ammonia set free, depending on the amount of buffer added.

The reaction mixture may be worked up, for example, by separating first the hydrogenation catalyst from the alkaline solution obtained, optionally after adding aqueous alkali, and precipitating subsequently the aminobenzimidazolone-(2) by the addition of an acid. However, other methods of work-up may also be considered.

The following passages give a detailed description of a particularly preferred embodiment of the process.

The crude moist dinitro-aryl urea or its derivatives described in Table I are introduced into water, to which a buffer adjusted to pH 6-7 (e.g. a phosphate buffer) and a small amount of active charcoal have suitably been added. The hydrogenation catalyst, for example nickel on kieselguhr, is added. Thereafter the mixture is rinsed successively with nitrogen and hydrogen and is heated under a pressure of 40 bars of hydrogen up to the start of the hydrogen absorption to a temperature in the range of from about 35° to 50° C. The reduction to give the diaminoaryl ureas is generally effected at a temperature of from about 50° to 80° C., especially from 55° to 60° C., under a pressure of 40 bars of hydrogen. After no hydrogen has been absorbed any more, the hydrogen is displaced by nitrogen. For the cyclization reaction to give the aminobenzimidazolones-(2), the reduction solution is brought to a temperature of from 100° to 150° C. Said reaction is completed after 2 to 10 hours, depending on the reaction temperature. By the splitting-off of ammonia, the reaction mixture is rendered alkaline (up to pH 10). It can be worked up according to various methods, depending on whether there are required catalyst-free aminobenzimidazolones-(2) for further treatment, or whether catalyst-containing products may be used.

Thus, for example, the catalyst-containing aminobenzimidazolones-(2) may first be separated from the mother liquor following a neutralization to pH 7, for example with hydrochloric acid, which products are then dissolved in an organic solvent, such as N-methylpyrrolidone, or diluted aqueous sodium hydroxide solution or in hydrochloric acid and subsequently filtered off from the catalyst.

The solutions in an organic solvent are appropriate, for example, for the immediate processing to obtain secondary products. It is also possible, however, to separate the aqueous alkaline reaction mixtures from the catalyst directly by filtration, preferably under heat, and to precipitate the aminobenzimidazolones-(2) from the filtrate by way of neutralization and isolate the same after a possible concentration, for example by filtration.

The aminobenzimidazolones-(2) obtained according to the process of the invention are valuable intermediates for the preparation of azo pigments.

The following Examples illustrate the present invention, the parts and percentages relating to the weight, unless otherwise stated.

EXAMPLES

1. 5-Aminobenzimidazolone-(2)

113 Parts of 2,4-dinitrophenyl urea are introduced into 3 liters of water, to which 8 parts of phosphoric acid and 8 parts of 33% sodium hydroxide solution have been added for buffering to pH 6. Thereafter 10 parts of active charcoal and 4 parts of nickel catalyst (55% of nickel on kieselguhr) are introduced. The suspension is hydrogenated at 40° to 60° C. and subsequently heated for 8 hours at 120° C. 60 Parts of 33% sodium hydroxide solution are added to the cooled reaction mixture which then is filtered while hot into 100 parts of 30% hydrochloric acid. The filtrate is concentrated in vacuo to 500 parts, the 5-aminobenzimidazolone-(2) is filtered off with suction, washed with ice water and dried in vacuo at 120° C. under nitrogen cover. There are obtained 64 parts of 5-aminobenzimidazolone-(2), melting point 234° to 236° C.

2. 5-Aminobenzimidazolone-(2)

The following components are placed into an autoclave having a capacity of 5 liters: 3000 parts of water, 16 parts of 85% phosphoric acid, 16 parts of 33% sodium hydroxide solution, 20 parts of active charcoal, 227 parts of 2,4-dinitrophenyl urea (1 mol) and 8 parts of nickel catalyst on kieselguhr. The suspension is hydrogenated at 30° to 60° C. in the autoclave. 15 Parts of sodium dithionite are added to the resulting reduction solution which then is separated from the catalyst. The filtrate is combined with 265 parts of 30% hydrochloric acid and is subsequently refluxed for 7 hours. The mixture ist then mixed with 136 parts of 33% sodium hydroxide solution, and the 5-aminobenzimidazolone-(2) is isolated at 5° C. by way of filtration. After drying in vacuo, there are obtained 121 parts of 5-aminobenzimidazolone-(2).

3. 5-Aminobenzimidazolone-(2)

The following components are placed into a 5 l autoclave: 3000 parts of water, 16 parts of 85% phosphoric acid, 16 parts of 33% sodium hydroxide solution, 20 parts of active charcoal, 227 parts of 2,4-dinitrophenyl urea and 1 part of catalyst (5% of palladium on carbon). The suspension is hydrogenated at 30° to 60° C. in the autoclave. To the resulting reduction solution 30 parts of sodium dithionite are added, and the resulting mixture is allowed to run into 265 parts of 30% hydrochloric acid and refluxed for 6 hours. Thereafter the mixture is clarified from the catalyst, while hot, and is mixed with 110 parts of 33% sodium hydroxide solution. The 5-aminobenzimidazolone-(2) precipitating in a crystalline form upon cooling is isolated at 5° C. by filtration. After drying in vacuo, there are obtained 121 parts of 5-aminobenzimidazolone-(2).

4. 2,4-Diaminophenyl urea

The reduction is carried out as has been described in Example 2, however, while isolating the 2,4-diaminophenyl urea in the form of its dihydrochloride. For this purpose, the reduction solution, after adding 15 parts of sodium dithionite, is clarified from the catalyst, and the filtrate is combined with 575 parts of 30% hydrochloric acid. The hydrochloric acid solution of the 2,4-diaminophenyl urea is concentrated in the vacuum of the water jet pump at 50° C. at a maximum to 650 parts of a white suspension and is mixed with 290 parts of 30% hydrochloric acid. The 2,4-diaminophenyl urea dihydrochloride having precipitated in a crystalline form is isolated at 5° C. by filtration and washed with 400 parts of 15% hydrochloric acid of 5° C.

After drying in vacuo at 50° C., there are obtained 197 parts of 2,4-diaminophenyl urea dihydrochloride in the form of white crystals. A further amount of 2,4-diaminophenyl urea dihydrochloride can be isolated from the mother liquor, besides small quantities of 5-aminobenzimidazolone-(2). The 2,4-diaminophenyl urea dihydrochloride may be cyclized in an aqueous solution, as has been described in Example 2, to yield 5-aminobenzimidazolone-(2).

Nuclear magnetic resonance spectrum of the 2,4-diaminophenyl urea dihydrochloride:
$\delta$(DMSO d$_6$):
8.5 to 9.5 ppm (broad signals, 9 H, N-H)
7.55 ppm (d, 1 H, H-6)
7.43 ppm (d, 1 H, H-3)
7.23 ppm (dd, 1 H, H-5)
Melting point: 184° to 187° C.

5. 5-Aminobenzimidazolone-(2)

100 Parts of needle iron cutting dust and 100 parts of iron filings are heated with 800 parts of water in the presence of 30 parts of acetic acid for 1 hour at a temperature of from 90° to 100° C. Thereafter 113 parts of 2,4-dinitrophenyl urea (0.5 mol) are introduced while stirring within 1 hour at 95° C., and the mixture is continued to be stirred for 2 hours at 95° C. under a nitrogen atmosphere. The pH value is adjusted to 8.5 at 90° C. by means of 50 parts of anhydrous sodium carbonate, and the mixture is then clarified from the iron oxide slurry by a pressure filter. Said iron oxide slurry is washed portionwise with 1000 parts of hot water. The filtrate is adjusted to a pH of 4.0 with 120 parts of 30% hydrochloric acid and is refluxed for 10 hours (pH 5.0). Thereafter the mixture is cooled and adjusted to pH 7.0 with 41 parts of 33% sodium hydroxide solution. The 5-aminobenzimidazolone-(2) precipitated in a crystalline form is isolated at 5° C. by filtration and washed with ice water. After drying in vacuo at 120° C., there are obtained 60 parts of 5-aminobenzimidazolone-(2).

6. 7-Chloro-5-aminobenzimidazolone-(2).

The following components are placed into a 5 l autoclave: 3000 parts of water, 23 parts of 85% phosphoric acid, 39 parts of 33% sodium hydroxide solution, 40 parts of active charcoal, 428 parts of 6-chloro-2,4-dinitrophenyl urea (1.64 mols) and 5 parts of nickel catalyst on kieselguhr. The reduction is executed as has been described in Example 1. After releasing the hydrogen pressure, the mixture is heated to 150° C., while stirring, and is continued to be stirred for 3 hours at this temperature. After the reaction solution has been cooled, the sparingly soluble 7-chloro-5-aminobenzimidazolone-(2) is filtered off together with the catalyst and washed with 2000 parts of water. The 7-chloro-5-aminobenzimidazolone-(2) is extracted from the mixture including charcoal and the catalyst by treating with 5 l of water and 230 parts of 30% hydrochloric acid at 50° C., and the resulting solution is clarified from the charcoal and the catalyst. From the filtrate, the 7-chloro-5-aminobenzimidazolone-(2) is precipitated with 450 parts of 25% ammonia at pH 9. The product is isolated at 50° C. by filtration and washed with 2000 parts of water. There are obtained 267 parts of 7-chloro-5-aminobenzimidazolone-(2) having a melting point of from 274° to 275° C.

7. 7-Methyl-5-aminobenzimidazolone-(2)

The following components are placed into a 1 l autoclave: 300 parts of drinking water, 1.6 parts of 85% phosphoric acid, 1.7 parts of 33% sodium hydroxide solution, 2 parts of active charcoal, 25 parts of 6-methyl-2,4-dinitrophenyl urea (0.10 mol) and 1.50 parts of nickel catalyst on kieselguhr. The reduction is effected as has been described in Example 1.

After releasing the hydrogen pressure, the mixture is heated to 120° C., while stirring, and is continued to be stirred at this temperature for 8 hours. The reaction solution is mixed with 2 parts of sodium dithionite, diluted with 100 parts of water, mixed with 25 parts of 33% sodium hydroxide solution (0.2 mol) and clarified from the catalyst at 90° C. in a nitrogen atmosphere. The catalyst is washed with 50 parts of hot 5% sodium hydroxide solution and then with hot water. Upon clarification, the filtrate is combined directly with 44 parts of 30% hydrochloric acid. From the filtrate, the 7-methyl-5-aminobenzimidazolone-(2) precipitates in a crystalline form. It is filtered off and washed with water. After drying in vacuo at 120° C., there are obtained 12.5 parts of 7-methyl-5-aminobenzimidazolones-(2) having a melting point of from 308° to 309° C.

8. 6-Methyl-5-aminobenzimidazolone-(2)

The components and their proportions as well as the execution of the process corresponds to Example 7, however, with the difference that instead of 6-methyl-2,4-dinitrophenyl urea there are used 25 parts of 5-methyl-2,4-dinitrophenyl urea. After drying in vacuo at 120° C., there are obtained 11 parts of 6-methyl-5-aminobenzimidazolone-(2), melting point 301° to 303° C.

9. 6-Methoxy-5-aminobenzimidazolone-(2)

The following components are introduced into a 2 l autoclave: 1000 parts of water, 8 parts of 85% phosphoric acid, 13.6 parts of 33% sodium hydroxide solution, 10 parts of active charcoal, 128 parts of 5-methoxy-2,4-dinitrophenyl urea (0.5 mol) and 4 parts of nickel catalyst on kieselguhr. The reduction is effected as in Example 1, but the hydrogen pressure is not released. The solution is heated to 150° C. and maintained at this temperature for 3 hours. The cooled reaction solution is mixed with 10 parts of sodium dithionite and adjusted to pH 7.0 with 35 parts of 30% hydrochloric acid. Subsequently the mixture is diluted with 2000 parts of hot water and clarified from the catalyst at 90° C. in a nitrogen atmosphere. The filtrate is concentrated in the vacuum of the water jet pump to about 500 parts. The 6-methoxy-5-aminobenzimidazolone-(2) having precipitated in a crystalline form is isolated at 5° C. by filtration and washed with 150 parts of ice water. After drying in vacuo at 120° C., there are obtained 62 parts of 6-methoxy-5-aminobenzimidazolone-(2), melting point 248° to 249° C.

10. 5-Amino-1-H-2-naphth[1,2-d]imidazolone

The following components are introduced into a 2 l autoclave: 750 parts of water, 4 parts of 85% phosphoric acid, 6.8 parts of 33% sodium hydroxide solution, 5 parts of active charcoal, 57 parts of 2,4-dinitronaphthyl urea (0.2 mol) and 3 parts of nickel catalyst on kieselguhr. The reduction is effected as has been described in Example 1. After releasing the hydrogen pressure, the mixture is heated to 150° C., while stirring, and is continued to be stirred for 3 hours at this temperature. The suspension is cooled to 25° C., adjusted to pH 7.0 by means of 16 parts of 30% hydrochloric acid and filtered. The sparingly soluble 5-amino-naphthimidazolone-(2) is dissolved at 90° C. in 3000 parts of water and 100 parts of 33% sodium hydroxide solution and clarified from the catalyst. Said catalyst is washed with 100 parts of hot 5% sodium hydroxide solution. The filtrate is adjusted to pH 7.0 with 115 parts of 30% hydrochloric acid, the 5-amino-naphthimidazolone-(2) having precipitated is filtered off at 25° C. and washed with water. After drying in vacuo at 120° C., there are obtained 26 parts of 5-aminonaphthimidazolone-(2), melting point 295° to 296° C.

11. 4-Aminobenzimidazolone-(2)

The following components are introduced into a 2 l autoclave: 600 parts of water, 3.2 parts of 85% phosphoric acid, 3.3 parts of 33% sodium hydroxide solution, 4 parts of active charcoal, 46 parts of 2,6-dinitrophenyl urea (0.2 mol) and 3 parts of nickel catalyst on kieselguhr. The reduction is effected as in Example 1. After releasing the hydrogen pressure, the mixture is heated to 120° C., while stirring, and stirring is continued for 8 hours at this temperature. The reaction solution is mixed with 5 parts of sodium dithionite and with 25 parts of 33% sodium hydroxide solution. Thereafter the mixture is clarified from the catalyst at 90° C. in a nitrogen atmosphere. Said catalyst is washed with 100 parts of hot 5% sodium hydroxide solution and then with hot water. Upon clarification, the filtrate is combined directly with 44 parts of 30% hydrochloric acid. The filtrate is concentrated to one third of its volume in the vacuum of the water jet pump. The 4-aminobenzimidazolone-(2) having precipitated in a crystalline form is isolated at 5° C. by filtration and washed with ice water. After drying in vacuo at 120° C., there are obtained 23 parts of 4-aminobenzimidazolone-(2), melting point 299° to 300° C.

What is claimed is:
1. A compound of the formula

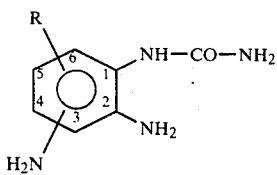

in which R is hydrogen, halogen, lower alkyl, lower alkoxy, phenyl, phenoxy or a fused benzene ring.

2. A compound as claimed in claim 1, wherein R is hydrogen, chlorine, methyl, methoxy or a fused benzene ring, and the second amino group is linked to the 6- or 4-position.

3. A compound as claimed in claim 2, wherein the second amino group is linked to the 4-position.

4. The compound as claimed in claim 3, wherein R is hydrogen.

5. The compound as claimed in claim 3, wherein R is 6-methyl.

6. The compound as claimed in claim 3, wherein R is 5-methyl.

7. The compound as claimed in claim 3, wherein R is 6-chloro.

8. The compound as claimed in claim 3, wherein R is 5-methoxy.

9. The compound as claimed in claim 3, wherein R is a benzene ring fused to the 5- and 6-positions.

10. The compound as claimed in claim 2, wherein R is hydrogen and the second amino group is linked to the 6-position.

* * * * *